United States Patent
Kar et al.

(10) Patent No.: US 10,788,373 B2
(45) Date of Patent: Sep. 29, 2020

(54) IMAGING DEVICE WITH LOOP BOLOMETER ARRAY AND RELATED METHODS

(71) Applicant: UNIVERSITY OF CENTRAL FLORIDA RESEARCH FOUNDATION, INC., Orlando, FL (US)

(72) Inventors: Aravinda Kar, Orlando, FL (US); Jeffrey Jennings, Melbourne, FL (US); Rajan Vaidyanathan, Orlando, FL (US)

(73) Assignee: UNIVERSITY OF CENTRAL FLORIDA RESEARCH FOUNDATION, INC., Orlando, FL (US)

(*) Notice: Subject to any disclaimer, the term of this patent is extended or adjusted under 35 U.S.C. 154(b) by 8 days.

(21) Appl. No.: 16/424,742

(22) Filed: May 29, 2019

(65) Prior Publication Data
US 2019/0368942 A1    Dec. 5, 2019

Related U.S. Application Data

(60) Provisional application No. 62/677,259, filed on May 29, 2018.

(51) Int. Cl.
| | |
|---|---|
| G01J 5/26 | (2006.01) |
| G01J 5/24 | (2006.01) |
| G01J 5/00 | (2006.01) |
| G01J 5/20 | (2006.01) |
| G01J 5/02 | (2006.01) |
| A61B 5/05 | (2006.01) |

(52) U.S. Cl.
CPC ............... *G01J 5/24* (2013.01); *A61B 5/05* (2013.01); *G01J 5/025* (2013.01); *G01J 2005/0077* (2013.01); *G01J 2005/202* (2013.01)

(58) Field of Classification Search
CPC ........ G01J 5/26; G01J 5/24; G01J 2005/0077; G01J 2005/202
See application file for complete search history.

(56) References Cited

U.S. PATENT DOCUMENTS

| | | |
|---|---|---|
| 2,590,477 A | 3/1952 | Weber |
| 5,055,288 A | 10/1991 | Lewis et al. |

(Continued)

OTHER PUBLICATIONS

Jennings et al. "Uncooled resistive metal foil bolometers for imaging with radiofrequency magnetic fields" http://mse.ucf.edu/ SPIE Defense + Commercial Sensing Conference, Orlando, FL; Session 4: Advanced Photodetectors and Bolometer [10656-13] Apr. 16, 2018; pp. 8.

(Continued)

*Primary Examiner* — Nicole M Ippolito
*Assistant Examiner* — Hanway Chang
(74) *Attorney, Agent, or Firm* — Allen, Dyer, Doppelt + Gilchrist, PA

(57) ABSTRACT

An imaging device may include an RF source configured to irradiate an object with RF radiation, and an array of RE antenna elements. Each RF antenna element may include a loop bolometer configured to receive the RF radiation after interaction with the object. The imaging device may include a processor configured to generate an image based upon respective outputs from the array of RF antenna elements, and a display coupled to the processor and configured to display the image of the object.

20 Claims, 17 Drawing Sheets

(56) References Cited

U.S. PATENT DOCUMENTS

| | | | |
|---|---|---|---|
| 5,777,329 | A | 7/1998 | Westphal et al. |
| 6,292,140 | B1 | 9/2001 | Osterman |
| 7,105,818 | B2 | 9/2006 | Anderson et al. |
| 8,080,779 | B2 | 12/2011 | Legras et al. |
| 8,080,793 | B2 | 12/2011 | Dupont et al. |
| 8,610,069 | B2 | 12/2013 | Swank et al. |
| 8,954,131 | B2 | 2/2015 | Weaver et al. |
| 2011/0204891 | A1 | 8/2011 | Drake et al. |

OTHER PUBLICATIONS

Fantom, A., "Radio frequency & Microwave Power Measurement" Peter Peregrinus Ltd., UK, 1990 pp. 73-98.

"Bolometers: Theory, Types and Applications" Torrence M. Walcott Ed. Nova Publishers, Inc., 2010.

Greene, Frank, M. "Near-Zone Magnetic Field of a Small Circular-Loop Antenna" Journal of Research of the National Bureau of Standards C. Engineering and Instrumentation, vol. 71C, 1967, pp. 319-326.

| Group | Sample Name | Position | Average radius (mm) | Offset from HHC centerline (mm) |
|---|---|---|---|---|
| Loop size | Thin SS 1 | Center (C) | 28.8 | 0.0 |
| | Thin SS 4 | C | 26.8 | 0.0 |
| | Thin SS 2 | C | 20.7 | 0.0 |
| | Thin SS 3 | C | 15.9 | 0.0 |
| | Thin SS 5 | C | 7.7 | 0.0 |
| Offset | Offset 1 | Offset (O) | 15.9 | 32.5 |
| | Offset 2 | O | 16.3 | 38.4 |
| | Offset 3 | O | 15.8 | 46.6 |
| Separation | Sep. 1 | C | 15.8 | 0.0 |
| | | O | 15.8 | 34.4 |
| | Sep. 2 | C | 15.8 | 0.0 |
| | | O | 15.9 | 46.1 |
| | Sep. 3 | C | 15.7 | 0.0 |
| | | O | 15.9 | 48.0 |
| Array | Element 1 | C | 16.0 | 0.0 |
| | Element 2 | O – upper left | 16.0 | 34.7 |
| | Element 3 | O – upper right | 15.7 | 33.9 |
| | Element 4 | O – lower right | 15.7 | 35.0 |
| | Element 5 | O – lower left | 15.9 | 34.3 |

FIG. 16

IMAGING DEVICE WITH LOOP BOLOMETER ARRAY AND RELATED METHODS

RELATED APPLICATION

This application is based upon prior filed Application No. 62/677,259 filed May 29, 2018, the entire subject matter of which is incorporated herein by reference in its entirety.

TECHNICAL FIELD

This present disclosure relates to imaging devices and, in particular, to radio frequency imaging devices and related methods.

BACKGROUND

In the imaging industry, there are several approaches to imaging an object of unknown internal structure. For example, these approaches comprise computed tomography (CT), positron emission tomography (PET), magnetic resonance imaging (MRI), ultrasound, acoustic microscopy, and conventional X-rays. The equipment used to provide such imaging is generally very complex and expensive. For CT imaging, the equipment may include a CT scanner that collects raw CT data and proprietary software that reconstructs 3D images out of raw data utilizing scanner's various hardware components, including computers.

SUMMARY

Generally, an imaging device may include a radio frequency (RF) source configured to irradiate an object with RF radiation, and an array of RF antenna elements. Each RF antenna element may include a loop bolometer configured to receive the RF radiation after interaction with the object. The imaging device may include a processor configured to generate an image based upon respective outputs from the array of RF antenna elements, and a display coupled to the processor and configured to display the image of the object.

In particular, the processor may be configured to generate the image of the object based upon detected spatial variation of flux density for the RF radiation. Each loop bolometer may be configured to receive the RF radiation emitted by the object during irradiation of the object with the RF source.

In some embodiments, each loop bolometer may comprise a resistive loop, and each RF antenna element may comprise a signal conditioning circuit coupled to the resistive loop. The signal conditioning circuit may be configured to pass a sensing current through the resistive loop. Each RF antenna element may comprise a capacitor coupled between ends of the resistive loop.

The signal conditioning circuit may comprise a plurality of resistors coupled as a resistor bridge. For example, the RF source may be configured to generate the RF radiation within a frequency range of 30 to 130 MHz. Also, each loop bolometer may be configured to receive the RF radiation emitted by the object without irradiation of the object with the RF source.

Another aspect is directed to an imaging device comprising an object configured to emit RF radiation, and an array of RF antenna elements, each RF antenna element comprising a loop bolometer configured to receive the RF radiation from the object. The imaging device may include a processor configured to generate an image based upon respective outputs from the array of RF antenna elements.

Yet another is directed to a method for making an imaging device comprising positioning an RF source configured to irradiate an object with RF radiation, and positioning an array of RF antenna elements. Each RF antenna element may include a loop bolometer configured to receive the RF radiation after interaction with the object. The method may comprise coupling a processor configured to generate an image based upon respective outputs from the array of RF antenna elements, and coupling a display to the processor and configured to display the image of the object.

BRIEF DESCRIPTION OF THE DRAWINGS

FIG. 16 is a table of sample names, relative location, and dimensions, grouped by experiment for example embodiments of the imaging device, according to the present disclosure.

DETAILED DESCRIPTION

Figure 1:
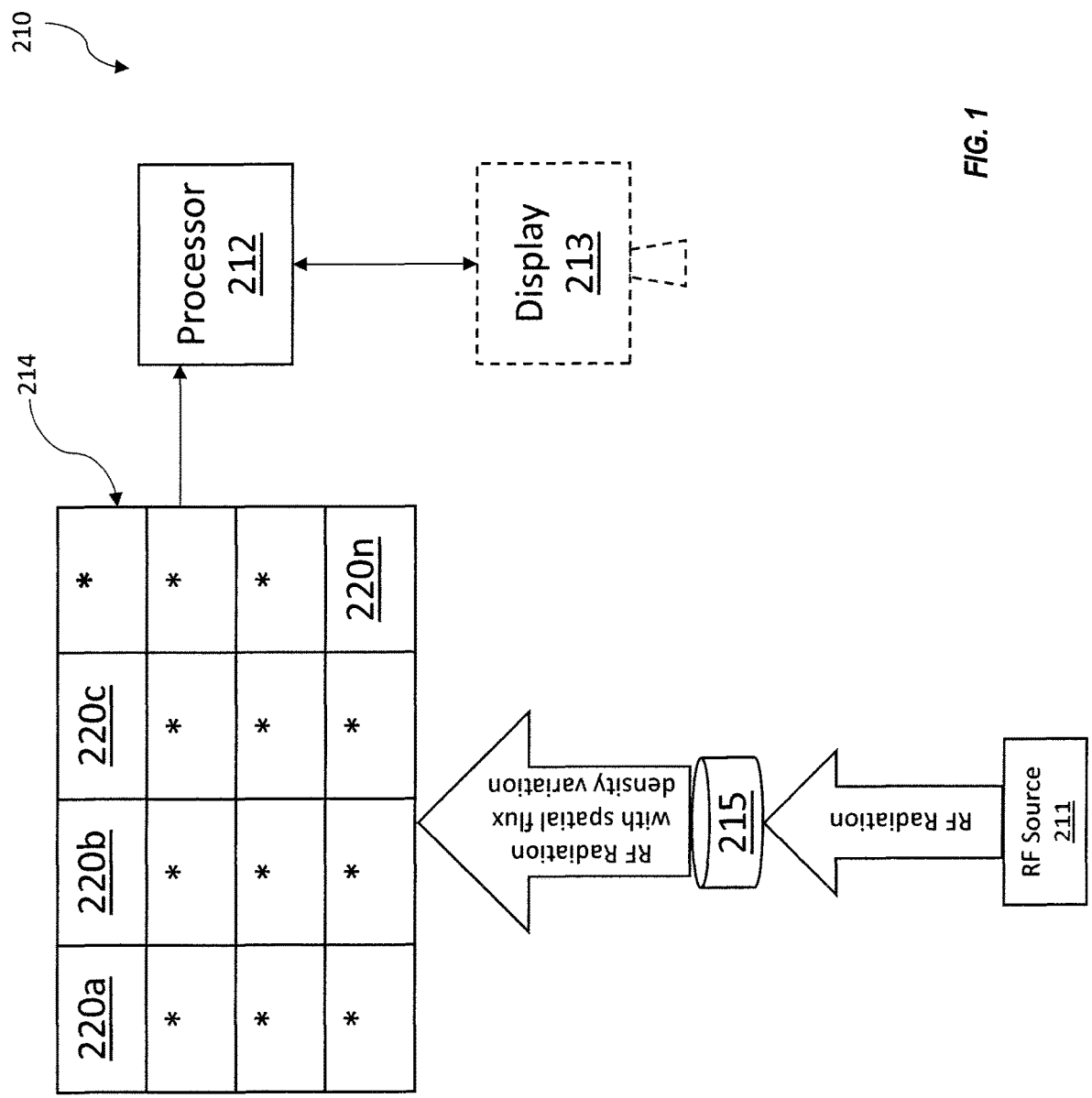
FIG. 1 is a schematic diagram of an imaging device, according to the present disclosure.

The present disclosure will now be described more fully hereinafter with reference to the accompanying drawings, in which several embodiments of the present disclosure are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Referring initially to FIG. 1, an imaging device 210 according to the present disclosure is now described. The imaging device 210 illustratively comprises an RF source 211 configured to irradiate an object 215 with RF radiation, and an array 214 of RF antenna elements 220a-220n. Each RF antenna element 220a-220n includes a loop bolometer configured to receive the RF radiation after interaction with the object 215. The imaging device 210 illustratively includes a processor 212 configured to generate an image based upon respective outputs from the array 214 of RF antenna elements 220a-220n, and a display 213 (shown with dashed lines, and can be omitted in some embodiments) coupled to the processor and configured to display the image of the object 215.

In particular, the processor 212 is configured to generate the image of the object 215 based upon detected spatial variation of flux density for the RF radiation. Each loop bolometer is configured to receive the RF radiation emitted by the object 215 during irradiation of the object with the RF source 211.

For example, the RF source 211 may be configured to generate the RF radiation within a frequency range of 30 to 130 MHz. Also, each loop bolometer may be configured to receive the RF radiation emitted by the object 215 without irradiation of the object with the RF source 211. In other words, in some embodiments, the RF source 211 may be omitted for a passive detection approach.

In the illustrated embodiment, for ease of illustration, the array 214 of RF antenna elements 220a-220n is shown as a square-shaped array with 16 elements. It should be appreciated that many embodiments of the array 214 of RF antenna elements 220a-220n would include a large number of RF antenna elements 220a-220n, for example, many thousands of RF antenna elements.

Briefly referring to FIGS. 4 and 12A-12D, several embodiments of the array 214 of RF antenna elements 220a-220n are shown. On example embodiment illustratively comprises a 5×5 square-shaped array 714. A second example embodiment illustratively includes a circle-shaped array 814 of RF antenna elements. A third example embodiment illustratively includes a circle-shaped array 914 of RF antenna elements with a different spacing. A fourth example embodiment illustratively includes a multi-level array 1014 of RE antenna elements with a different vertical spacing. A fifth example embodiment illustratively includes an array 1114 of RE antenna elements with a different lateral spacing.

Yet another is directed to a method for making an imaging device 210 comprising positioning an RF source 211 configured to irradiate an object 215 with RF radiation, and positioning an array 214 of RF antenna elements 220a-220n. Each RE antenna element 220a-220n includes a loop bolometer configured to receive the RF radiation after interaction with the object 215. The method comprises coupling a processor 212 configured to generate an image based upon respective outputs from the array 214 of RF antenna elements 220a-220n, and coupling a display 213 to the processor and configured to display the image of the object 215.

Figure 2:
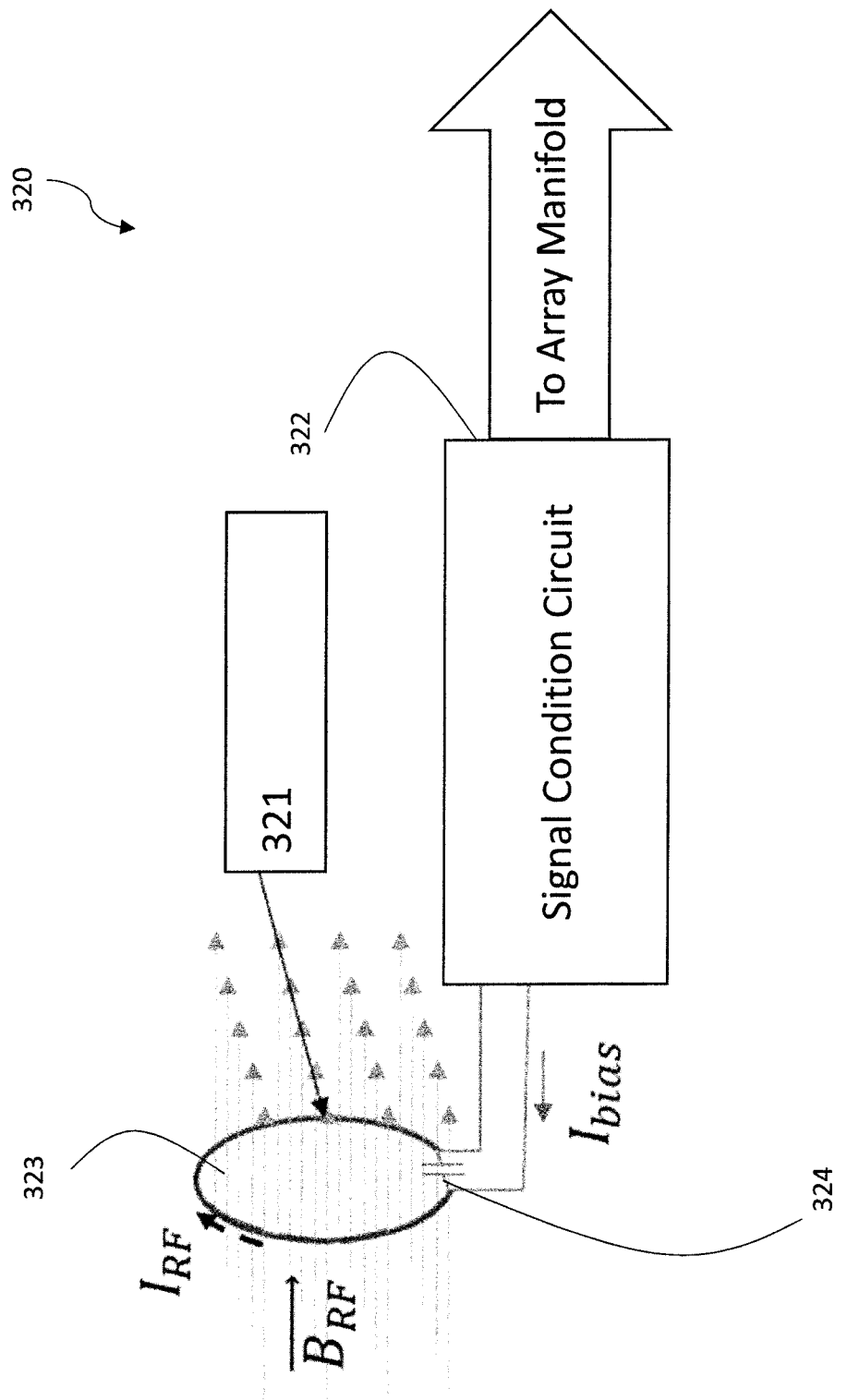
FIG. 2 is a schematic diagram of another embodiment of the imaging device, according to the present disclosure.
Figure 3:
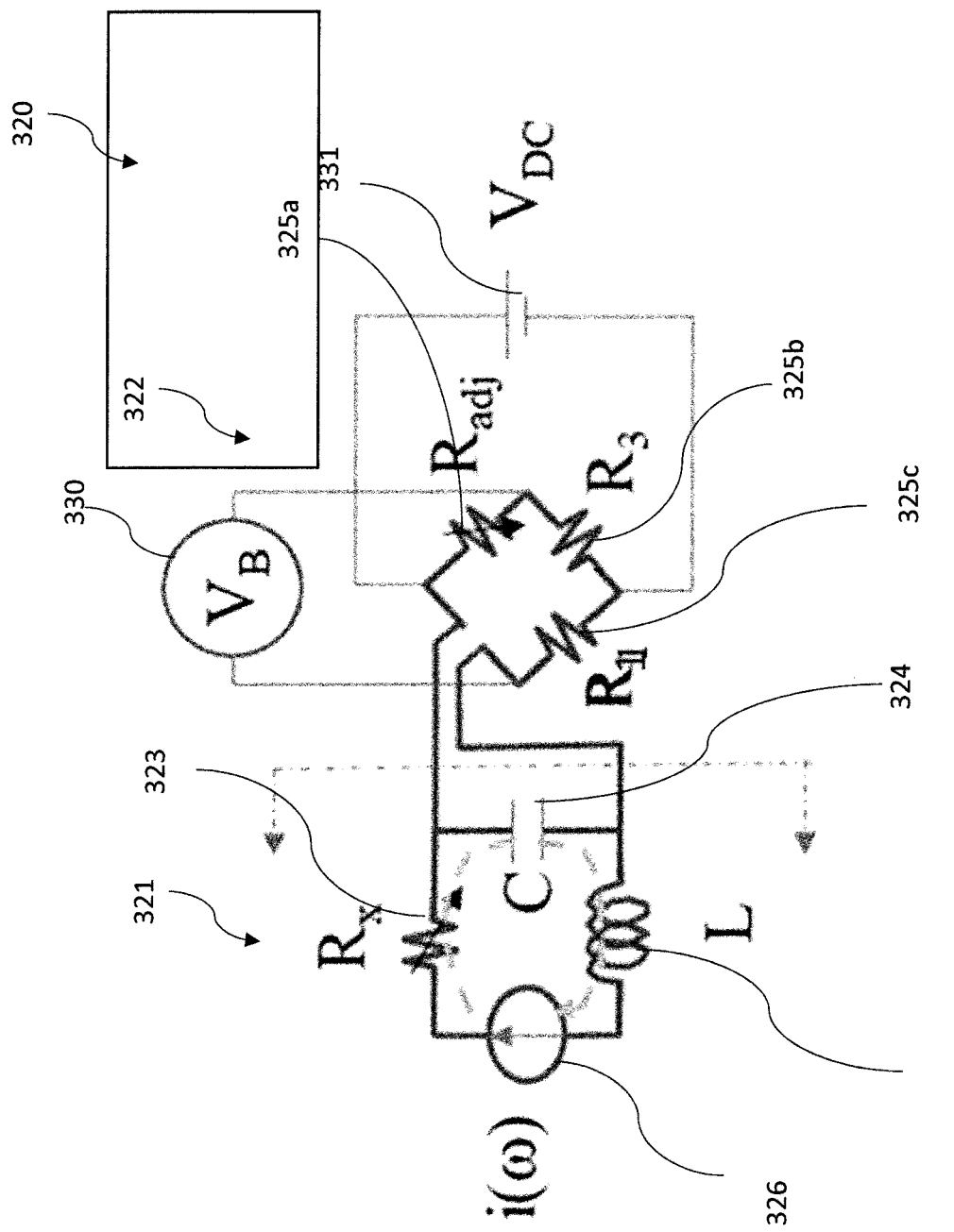
FIG. 3 is a schematic diagram of the RF antenna element and signal conditioning circuit from the imaging device of FIG. 2.
Figure 4:
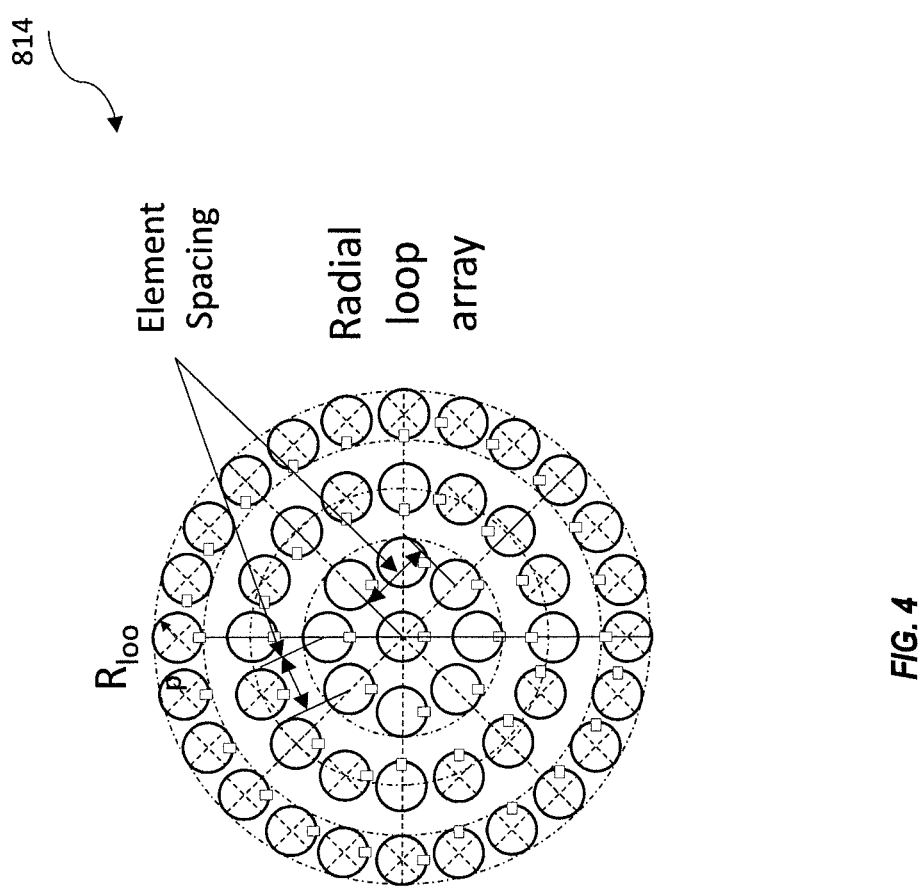
FIG. 4 is an example embodiment of the array of RF antenna elements from the imaging device, according to the present disclosure.

Referring now additionally to FIGS. 2-3, another embodiment of the imaging device 310 is now described. In this embodiment of the imaging device 310, those elements already discussed above with respect to FIG. 1 are incremented by 100 and most require no further discussion herein. This embodiment differs from the previous embodiment in that this imaging device 310 illustratively has each loop bolometer 321 comprising a resistive loop 323. The resistive loop 323 may comprise a loop-shaped, thermo-sensing element of a resistive material (e.g., metal, semiconductor, other) with a known temperature coefficient of resistance (TCR) and support structure. Also, the resistive loop 323 is illustratively circle-shaped, but may comprise other closed loop shapes, such a square-shape, for example.

Each RF antenna element 320 illustratively includes a signal conditioning circuit 322 coupled to the resistive loop 323. The signal conditioning circuit 322 is configured to pass a sensing current through the resistive loop 323. Each RF antenna element 320 illustratively comprises a capacitor 324 coupled between ends of the resistive loop 323.

The signal conditioning circuit 322 illustratively includes a plurality of resistors 325a-325c coupled as a resistor bridge (e.g. a Wheatstone bridge), a power supply voltage source 331 coupled between first and second legs of the resistor bridge, and a voltage meter 330 coupled between second and third legs of the resistor bridge. The plurality of resistors 325a-325c illustratively comprises an adjustable resistor 325a.

The loop bolometer 321 illustratively includes the resistive loop 323 and an inductive element 327. The loop bolometer 321 generates a current 326 when receiving RF radiation.

Figure 5:
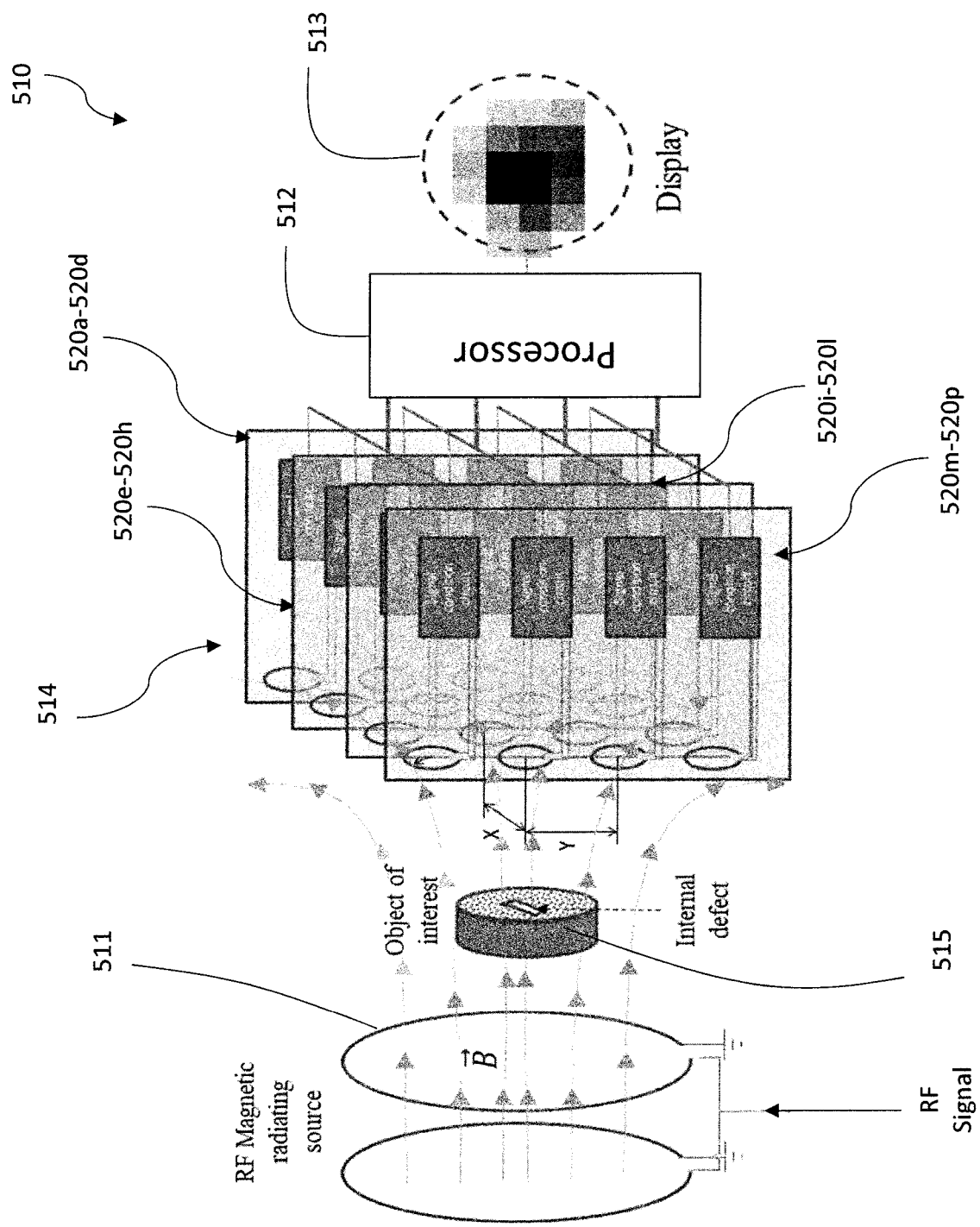
FIG. 5 is a schematic diagram of another embodiment of the imaging device, according to the present disclosure.

Referring now additionally to FIG. 5, another embodiment of the imaging device 510 is now described. In this embodiment of the imaging device 510, those elements already discussed above with respect to FIG. 1 are incremented by 300 and most require no further discussion herein. This embodiment differs from the previous embodiment in that this imaging device 310 illustratively comprises a HHM coil as the RF source 511. In this embodiment, the array 514 of RF antenna elements 520a-520p each illustratively comprises a loop bolometer and a signal conditioning circuit 322 coupled thereto.

Figure 6:
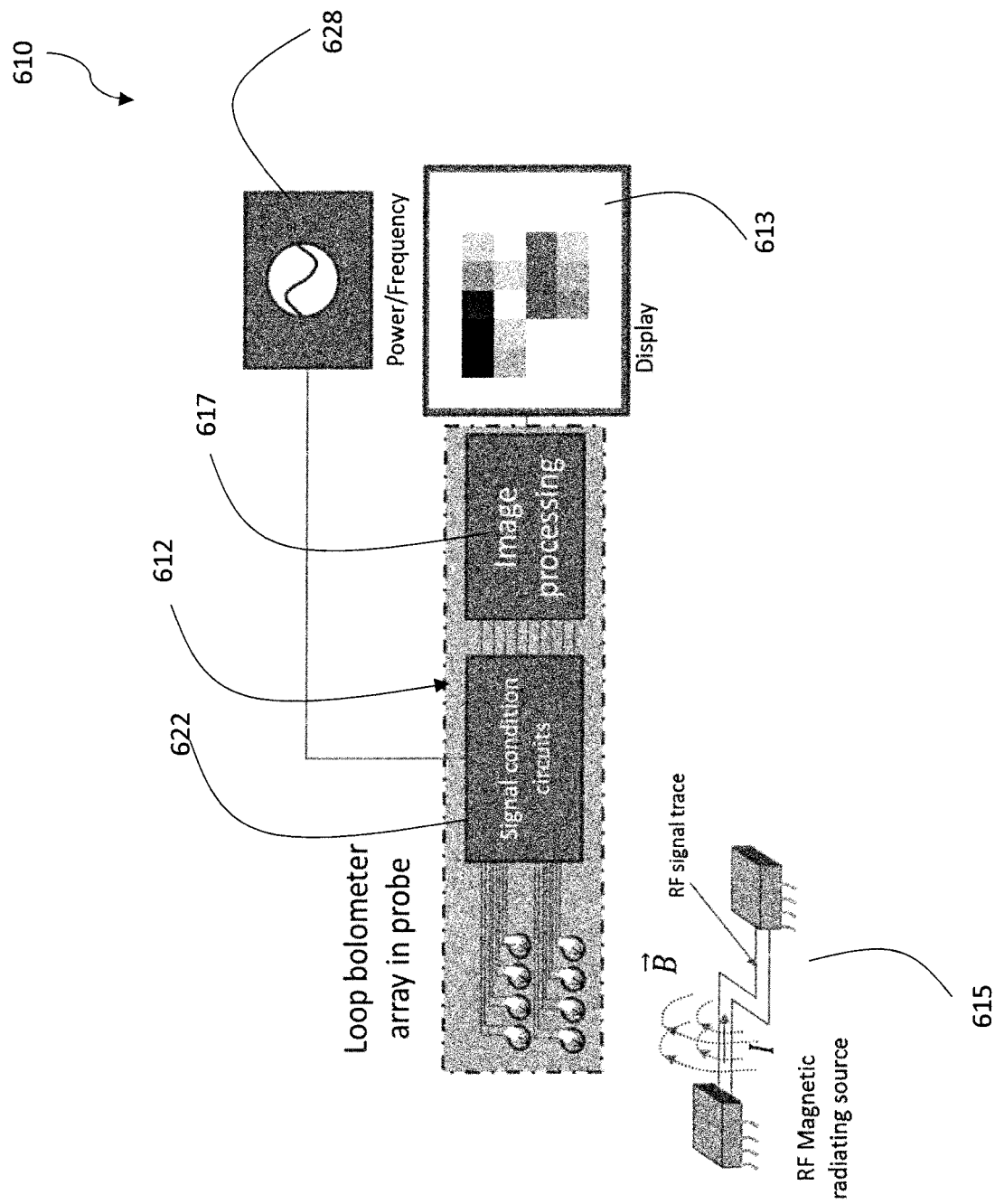
FIG. 6 is a schematic diagram of yet another embodiment of the imaging device, according to the present disclosure.

Referring now additionally to FIG. 6, another embodiment of the imaging device 610 is now described. In this embodiment of the imaging device 610, those elements already discussed above with respect to FIG. 1 are incremented by 400 and most require no further discussion herein. This embodiment differs from the previous embodiment in that this imaging device 610 illustratively has the processor 612 comprising an integrated signal conditioning circuit 622 and an integrated image processing circuit 617. The imaging device 610 illustratively includes a power circuit 628 coupled to the integrated signal conditioning circuit 622.

This imaging device 610 illustratively operates in a passive mode, and the object 615 is the RF magnetic radiating source field source, thereby omitting the separate RF source. Indeed, the object 615 is an integrated circuit device in an energized state.

Figure 13:
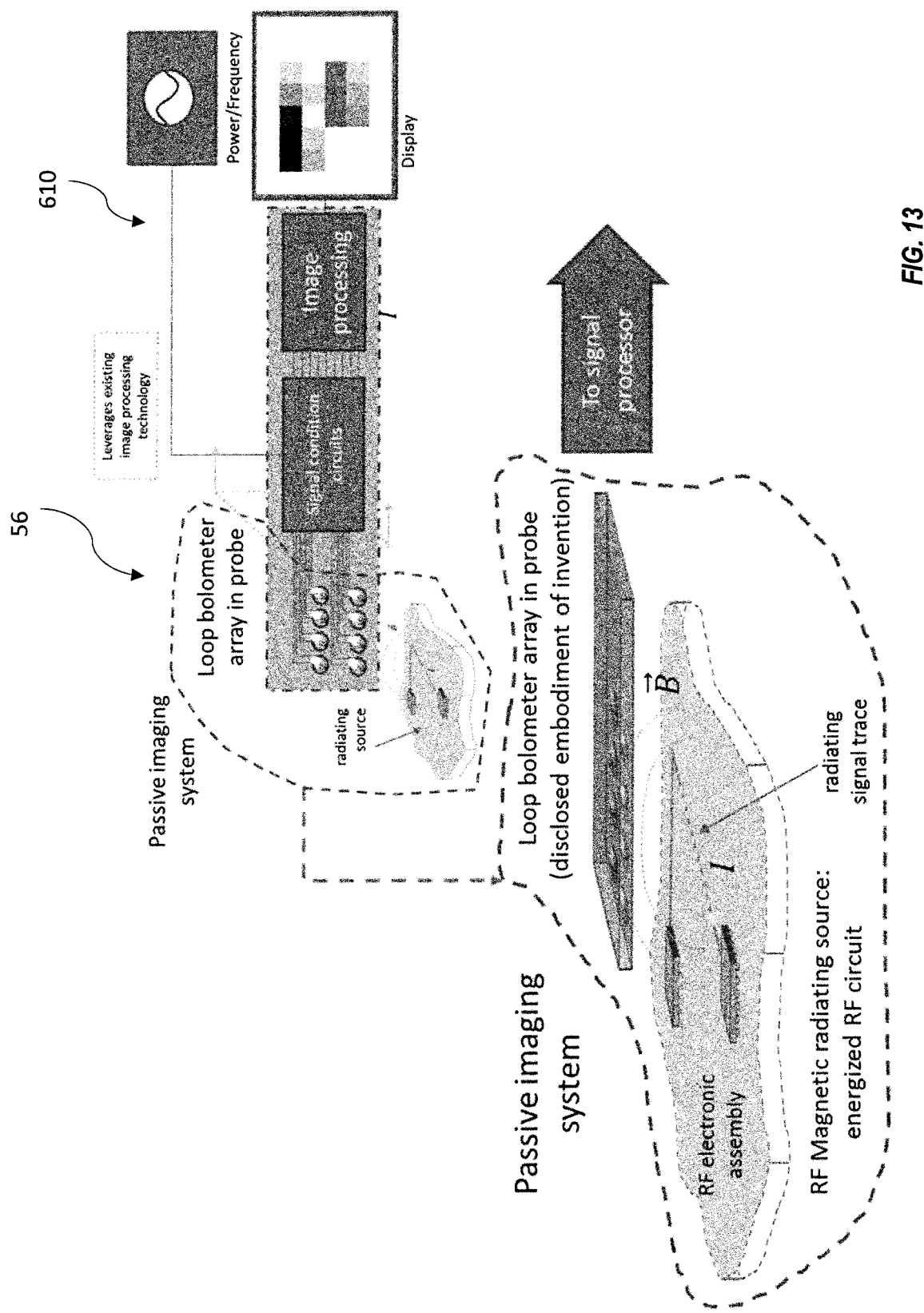
FIG. 13 is a schematic diagram of the imaging device in a passive mode, according to the present disclosure.
Figure 14:
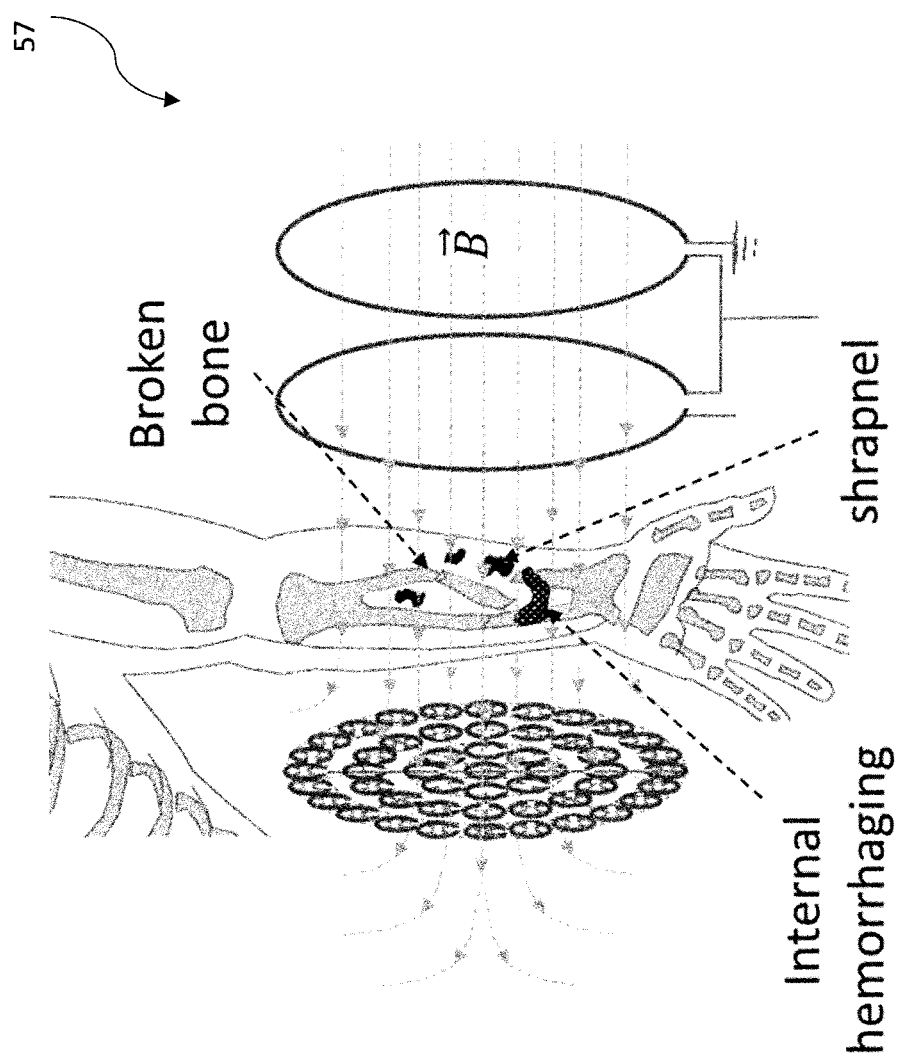
FIG. 14 is a schematic view of the imaging device used as a medical imager, according to the present disclosure.
Figure 15:
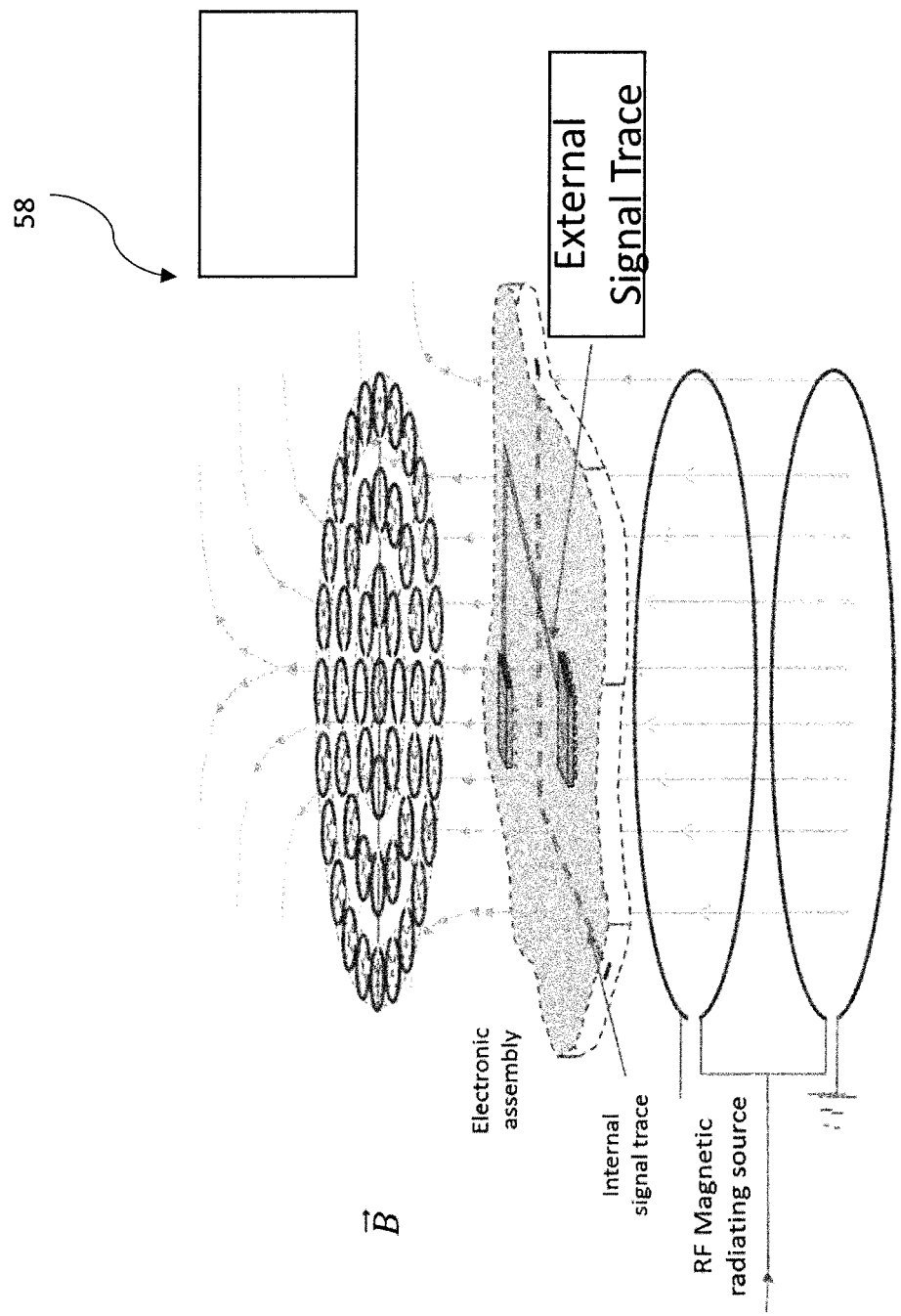
FIG. 15 is a schematic view of the imaging device used for electronic circuit non-destructive analysis, according to the present disclosure.

Referring briefly to FIGS. 13-15, a diagram 56 shows an exemplary application of the imaging device 610 (FIG. 6). The imaging device 610 is shown in an application for passive imaging of an RF electronic assembly. Diagram 57 shows an exemplary medical imaging application. Diagram 58 shows an exemplary electronic circuit non-destructive analysis application.

In the following, a first exemplary discussion of example embodiments of the present disclosure now follows.

Introduction

The bolometer has remained a relevant sensor technology because of its high sensitivity and flexibility in design [1, 2]. Early implementations for RF power measurement included resistive bolometers often situated within waveguides or similar RF resonant structures to increase the electromagnetic signal incident on the sensor [3, 4]. Later, the incorporation of uncooled-resistive bolometers into arrays proved an effective implementation for producing infrared imaging [5]. The present disclosure includes an imaging technique based on an uncooled-resistive loop bolometer design, which in an array configuration intends to produce images from radiated RF magnetic fields [6]. The technique relies on the same types of matter-magnetic field absorption interactions that occur during magnetic resonance imaging (MRI), but the manner for producing an image is distinct. MRI and many other nuclear magnetic resonance methods utilize a large static magnetic field to hyper-polarize nuclei of atoms within the object prior to imaging, displaces those aligned protons with an RF magnetic pulse and uses a large detector coil to detect the signal produced by the displaced atoms' return to alignment [7]. The spatial location of a pixel is determined by a superimposed spatial encoding signal [8, 9]. The present disclosure creates an image from the spatial variations of flux density for an incident RF magnetic field detected at each loop sensor location within the array located downstream from the object positioned within a known RF magnetic field. The RF magnetic flux at the individual elements depends on the amount of attenuation occurring as it passes through the object region in each element's field of view. Individual detector field strength measurements are then converted into a contrast value that is then spatially displayed to produce a "magnetic image." A notional imaging system configuration is shown in FIG. 5.

The imaging device 510 in FIG. 5 illustratively comprises a RF magnetic field source 511, a sample region 515, the loop bolometer detector array 514 with signal conditioning, image processing 512 and a display 513. The notional RF magnetic field source 511 shown is a Helmholtz coil driven with a RF signal at frequencies known to interact with the objects of interest. The frequency range initially proposed is based on the range used in traditional MRI in the range of 10 to 130 MHz [10].

The loop bolometer design, which acts as the sensor, is shown in FIG. 2. The loop bolometer design illustratively includes a single or multi-closed-loop element 321 constructed from a material with high temperature coefficient of resistance (TCR) coupled with a signal conditioning circuit 322, which enables detection of the small resistance changes occurring within the loop 323 caused by the RF magnetic field induced current-generated Joule heating. A notional schematic of a bridge circuit for signal conditioning circuit 322 and how the loop bolometer could be interconnected is shown in FIG. 3. The loop portion 321 on the circuit will likely include an RF coupling capacitor 324 or quarter wave stub to cause it to behave like a conductive closed-loop with the intent to minimize the amount of RF current that enters the signal conditioning circuit 322.

The primary performance characteristics for this imaging system are resolution and contrast. The main design parameter determining the minimum resolution possible is the separation between adjacent loop sensors. The primary factor affecting the range of contrast possible is the RF magnetic flux change detection limit of the loop bolometer element. The TCR of the loop material and capabilities of the bridge circuit design are primary factors affecting this limit, while the characteristics of the loop element array also play a key role. Loop size directly impacts the amount of the incident RF magnetic flux that a single element detects and the separation between adjacent elements and their tendency to mutually couple also contribute. In addition, the RF source type and location of the loop element with respect to that RF source impact the RF magnetic flux available for detection. In order to examine how these loop element array characteristics may affect the proposed imaging system, a series of experiments were conducted which aim to show how loop size, loop location, and loop-to-loop separation may impact the performance of a loop element individually and in an array. Furthermore, a small element count loop array was used to demonstrate the transmissive RF magnetic imaging technique for a simple object.

Experimental Methods

The operation of the disclosed loop bolometer element is simulated experimentally by soldered, circular, closed-loop wire rings with a thermocouple attached. The closed-loop samples were fabricated using 0.130 mm diameter, 300-series stainless steel (SS) wire twisted and attached with 91 wt % tin-9 wt % zinc solder. The relatively low conductivity value, 1.4 μS/m, of the stainless steel wire ensures a significant temperature rise for the magnetic field conditions applied during the experiment. The loop samples are mounted on a flat cardboard card with adhesive tape shown not to affect the RF magnetic field. A K-type thermocouple is positioned in contact with the closed wire loop. Thermal paste is applied at the wire-to-thermocouple tip interface to improve the coupling between them since the thermocouple tip is larger than the wire diameter. The thermocouple output is displayed on a digital thermal couple reader with 0.1° C. resolution and ±0.1%+0.6° C. accuracy. The loop size group of samples include single closed-loops fabricated with radius values ranging from 7 to 29 mm positioned so that their center is collocated with the HHC center axis when placed in the test position. The offset samples were closed loop samples at the same radius value as thin SS 3 sample placed with their loop center at a certain offset distance away from the HHC center axis when in the test position. The separation (Sep.) samples combine two closed-loop samples together, positioned with one loop (C) coaxially located at the HHC center and the other in an offset (O) position. The Array sample includes 5 close loop elements, 1 located at the HHC center axis position and the other loops located at similar offsets, but evenly separated radially around the center loop. A list of the samples and their dimensions are listed in the table of FIG. 16.

The RF source used for these experiments is a shielded HHC, which has been optimized to radiate at peak efficiency near 65 MHz. The two single turn loops that make up the coil (HHC 1 and HHC 2) are 100 mm in diameter, separated by 50 mm. When radiating, a RF signal generator produces a −16 dBm, 65 MHz continuous sinusoidal signal that gets amplified by 59±3 dB using a high-power RF amplifier prior to injection directly into the input of the HHC. This generates a RF magnetic field with peak flux density values in the proximity of the HHC near 14 μT which matches the peak RF conditions used during typical 1.5 T MRI[9]. While testing is underway, the RF magnetic field strength is monitored using the output of a 50 mm diameter shielded receive loop antenna located coaxially at 76.2 mm from the HHC centerline (25 mm inboard from each HHC loop) displayed on a spectrum analyzer. A thermocouple is positioned near the receive loop to monitor the air temperature adjacent to the sample location.

Prior to temperature rise measurements, the effect of a sample on the receive loop output was characterized. This was accomplished by measuring the detected peak magnetic field strength with and without the sample present in the field. This measurement is later used to calculate the applied magnetic field strength value from the field strength measurements taken during temperature rise experiments.

The temperature-rise experiment includes measuring the initial loop(s) and ambient temperatures, energizing the HHC coil, recording the peak RF magnetic field strength while the sample achieves steady state temperature, then deenergizing the HHC and immediately recording the sample and ambient temperature readings. Removal of the RF signal was necessary during temperature measurements because the RF signal interferes with the digital thermocouple reader output. During measurements, the closed-loop samples are positioned perpendicular to the HHC axis in a plane 57.2 mm from the HHC centerline where the desired RF magnetic field strength conditions are achieved. The RF magnetic field was applied for 10 minutes with the measurement repeated a minimum of 3 times for each sample.

Figure 7:
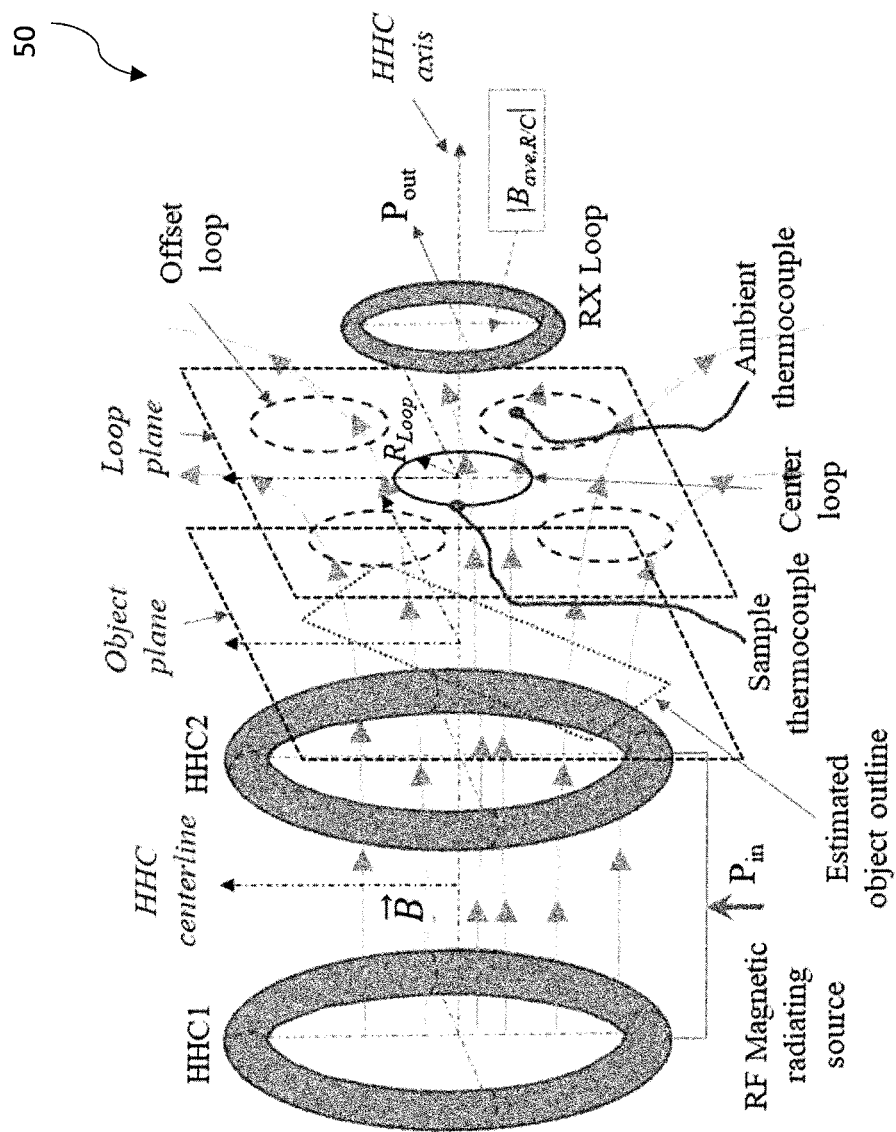
FIG. 7 is a diagram of an expanded view of temperature rise experimental setup showing relative positions of loop plane and object planes with respect to the RF source and receive coils in the imaging device, according to the present disclosure.

To demonstrate the magnetic field imaging technique, temperature rise measurements with and without an object present were compared. The object used for imaging was a 25 mm×65 mm×1.6 mm thick 2024 aluminum sheet. Steady state baseline, "no object" temperature-rise measurements were recorded using the same approach described previously. The aluminum piece was then placed in the "object plane" perpendicular to the HHC center axis located~50 mm from the HHC centerline in such a way as to screen portions of the array to varying degrees. The "with object" temperature rise in the array were then recorded again to see how the temperature rise was altered at each element by the object's presence. That percent change was then assigned a scaled contrast value for pixels situated in the same orientation as the loop element array to form the image. An expanded view of the experiment and the relative position of the different elements are shown in diagram 50 FIG. 7.

Results and Discussion

Figure 8:
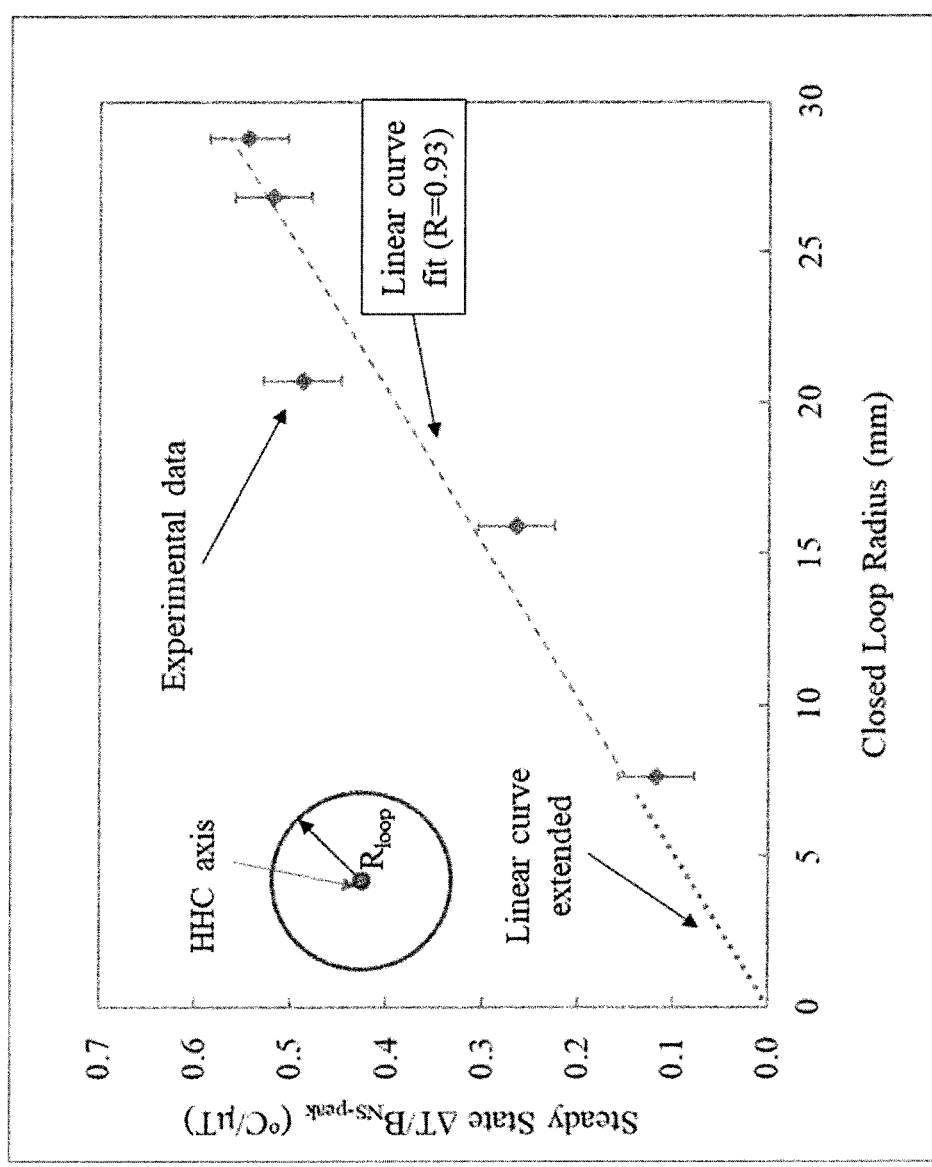
FIG. 8 is a diagram of flux normalized temperature versus loop radius in the imaging device, according to the present disclosure.
Figure 9:
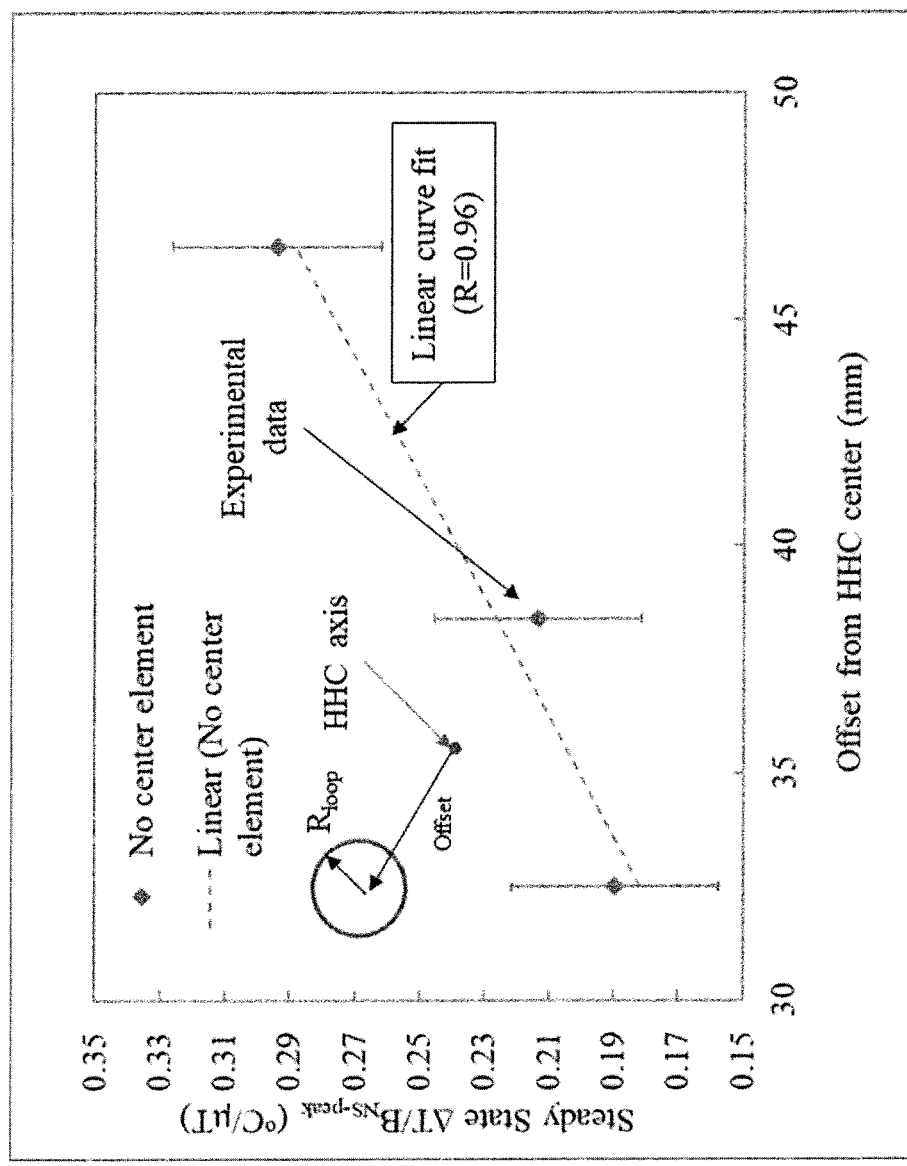
FIG. 9 is a diagram of flux normalized temperature rise versus offset of element from a Helmholtz coil (HHC) source center axis for loop element in the imaging device, according to the present disclosure.
Figure 10:
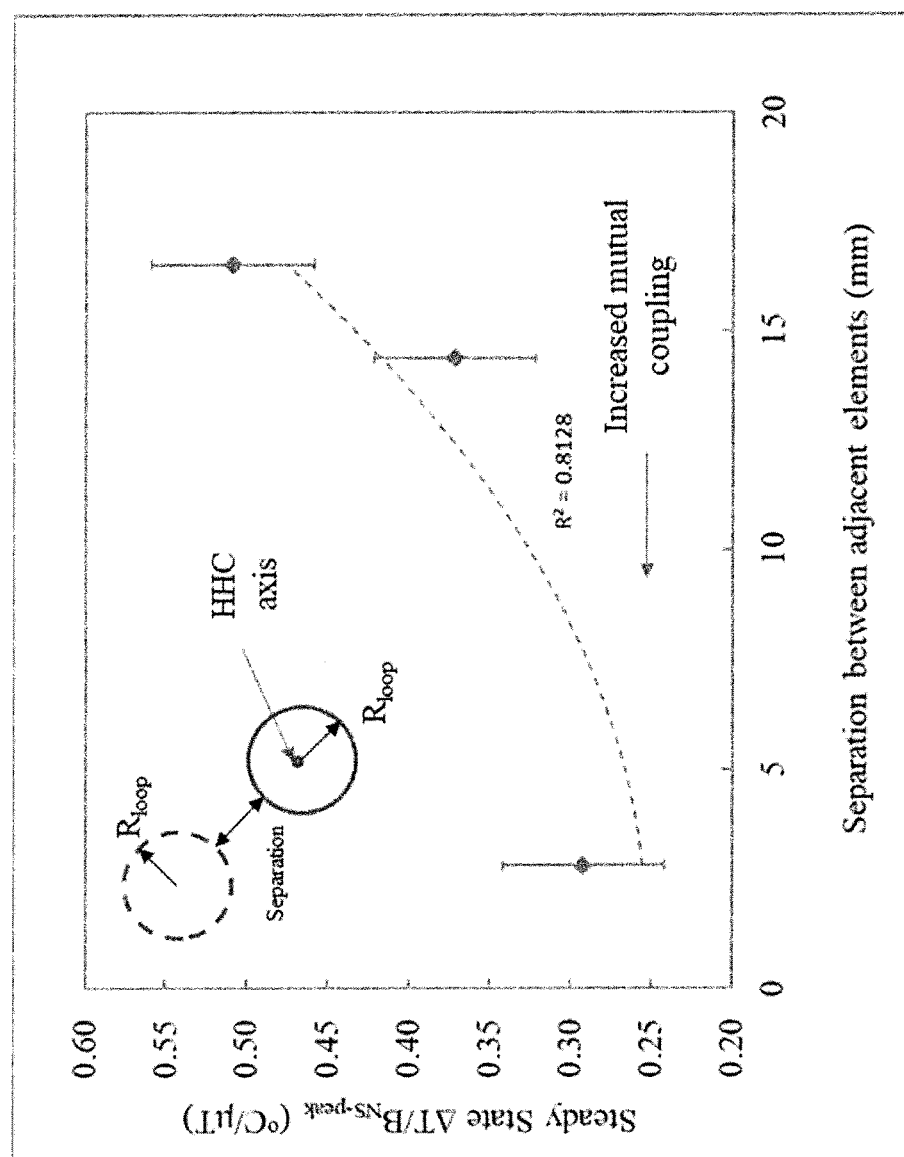
FIG. 10 is a diagram of flux normalized temperature rise versus separation to offset element for a center element in the imaging device, according to the present disclosure.

Temperature rise results for various loop sizes, offsets from the HHC center axis, and loop pair separation are shown in FIGS. 8-10. The temperature rise measurements in each diagram 51-53 were adjusted due to the slight temperature rise occurring in the thermocouple due to interaction with the RF magnetic field. This adjustment was based on the changes observed in the thermocouple monitoring the ambient temperature conditions during each temperature rise measurement. Due to changes in gain provided by the RF high power amplifier during testing at different ambient conditions, it was also necessary to normalize the temperature rise measurements to account for the resultant variations in the radiated RF magnetic field strength. This was accomplished by finding the proportionality constant for a zero-intercept linear curve fit between the average RF magnetic field flux density and the steady state temperature rise results for each data set. Those constants were then used in the various comparisons presented. The normalized temperature rise results for different closed-loop sizes shown in FIG. 8 reveal a direct linear relationship with loop size, as expected. Utilizing these results, it is possible to project down to an element size at the limit of resolution. Using the current test configuration, with an element fabricated with a material with a reasonable TCR value of 0.003Ω/° C. and an applied 14 μT RF magnetic field the current results predict the smallest element size that would produce a detectable change using conventional analog circuitry with a 10 ppm resistance resolution would have a radius on the order of ~13 μm [3, 11]. Increasing the TCR value to those achieved by more advances bolometer thermosensing materials like polycrystalline Si—Ge films with a 2%/° C. TCR could further reduce the element size threshold down approaching an approximate 2 μm radius [12].

FIG. 9 shows the effects of moving the closed-loop element away from the HHC center axis but remaining within the radius of the HHC coil radius at 50 mm. As the normalized temperature rise versus separation from the HHC axis data indicates, the temperature rise increases nearly linearly as the amount of separation increases. This result is most likely due to the close proximity of the loop plane with respect to the HHC loop. With a physical separation of only 25 mm, it is likely that the increased temperature rise is caused by the strong mutual coupling occurring between the closed wire loop samples and the closer of the two HHC coils.

The normalized temperature rise data shown in FIG. 10 reveals the effect of bringing two elements into close proximity. As the separation between the offset element and the center element is reduced, the temperature rise in the center element is decreased exhibiting the increased impact of mutual coupling which is resulting in RF magnetic field cancellation in the near field around each closed-loop element under non-resonant conditions. The nearly parabolic behavior with separation is consistent with the relationship between the separation and induced coupling between loop element pairs [13].

Figure 11B:
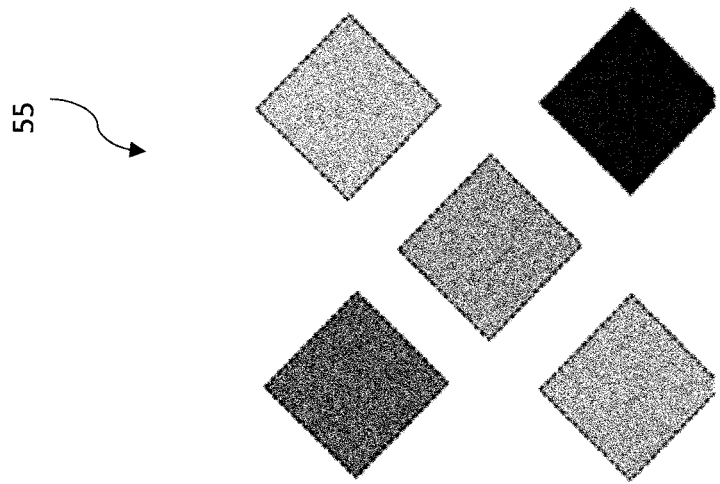
FIGS. 11A-11B are coarse array and gray scale map diagrams, respectively, of a contrast map based on temperature change caused by object placed between HHC source and loop element array in the imaging device, according to the present disclosure.
Figure 11A:
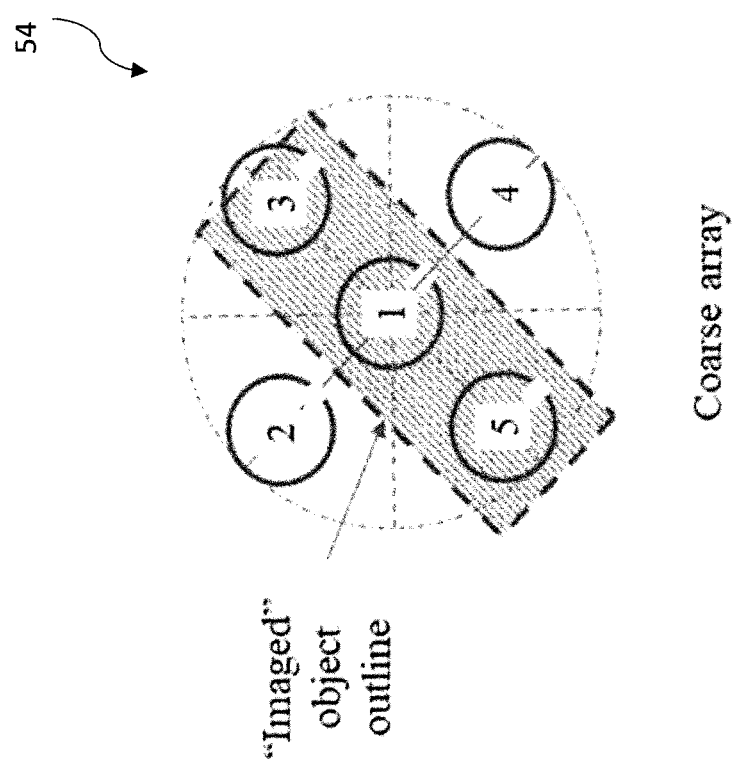

Lastly, FIGS. 11A and 11B (diagrams 54, 55) show the approximate location of the object with respect to the elements in the array along with the resultant magnetic image produces using the changes in temperature rise at each array element. The contrast values shown were based on changing the transparency value to match the percent change in temperature for pixels of the same color. As the image indicates elements 2 and 4, which have mostly unobstructed incident RF magnetic fields, had only minimal changes in temperature rise maintaining their original gray scale color while the changes in temperature drop for the elements screened by the object were far more significant resulting in pixels with much lighter gray shading values. As this result confirms, imaging objects with RF magnetic fields is possible and warrants further development.

CONCLUSIONS

The present disclosure presents the results for various experiments with the intend of evaluating how loops within an array interact when in the presence of an incident RF magnetic field for the purpose of characterizing how these interactions may impact the performance of novel bolometer loop elements configured in an array used in generating images from the interaction of objects with incident RF magnetic fields. The results indicate that achievement of an element size, which provided a reasonable image resolution, but that mutual coupling between elements in close proximity may degrade that performance. Variations observed for the offset samples also indicate that the geometry, type and strength of the RF source will play an important role in determining the magnetic flux density across the array plane.

In the following, a second exemplary discussion of example embodiments of the present disclosure now follows. An imaging device may illustratively includes an RF source configured to irradiate an object with radiation, and an array of RF antenna elements. Each RF antenna element may have a loop bolometer configured to receive residual RF radiation after interaction with the object. The imaging device illustratively includes a processor configured to generate an image based upon respective outputs from the array of RF antenna elements, and a display coupled to the processor and configured to display the image of the object.

In some embodiments, each loop bolometer comprises a resistive foil loop and signal conditioning circuitry. The loops receive RF magnetic fields generated by the RF source which may be within a frequency range of 30 to 100 MHz.

The disclosure provides an imaging system comprising a loop-shaped, resistive foil bolometer detector array, which receives an RF magnetic field from some transmitting source. The local flux density at a particular loop element induces current within the loop causing Joule heating that results in a detectable resistance change within a bolometer circuit. In an alternative configuration, the induced current is directly amplified to provide the analog signal used to produce an image. That output is converted to a pixel intensity, which is then combined spatially with the remaining elements to produce a composite image. Images of the detector's surroundings near operating electronics characterize the inductive environment present; while an object with favorable electromagnetic properties and geometry placed within the transmit path of the sourced RF magnetic field affects the relative magnetic field strength incident upon individual array elements altering the relative pixel intensities creating its "magnetic" image.

The disclosed embodiments comprise an imaging system having an uncooled, loop-shaped, resistive (micro-) bolometer detector array, which receives an RF magnetic field from some transmitting source which after interaction with the imaged object causes spatially varying flux density at the elements enabling conversion into an image. See FIG. 5 for schematic representation of an imaging system containing conceived elements within the proposed imaging system. The imaging system's major components include a RF magnetic field radiator, a loop-shaped bolometer detector array, an image processor, and a display.

The RF magnetic field radiator is the source of the RF magnetic field used to produce an image. Its configuration within the imaging system defines the mode of operation. In the active mode, an antenna structure with known RF magnetic field radiating properties, like a shielded loop antenna or Helmholtz Coil, positioned adjacent to the object of interest is excited at a desired frequency and output power to produce the imaging RF magnetic field. The radiating frequencies intended for this application are similar to those used in nuclear magnetic resonance imaging in the range of, but not limited to: 30-100 MHz. These frequencies are desirable, due to their ability to penetrate a wide variety of material types. The radiated RF magnetic field lines pass through the object and cause the atomic and/or molecular magnetic moments to rotate with respect to the direction of the field lines.

Also, free electrons within the object will tend to revolve around the field lines in induced eddy currents. Because the RF field strength and direction are continuously changing, these motions vary constantly with the net effect of reducing the field line's strength as it passes through the object. The extent of this change in field strength depends on the electromagnetic properties and geometry of the imaged object. Dielectric materials, due to their lack of free electrons and magnetic moments, have little effect on the field strength transmission. In diamagnetic and paramagnetic conductors, the electron flow likely contributes to the most significant RF magnetic energy absorption. For ferromagnetic materials (e.g., anti-ferromagnetic, ferrimagnetic, and ferromagnetic), the RF magnetic absorption should be maximized since both eddy currents and atomic/molecular magnetic dipole shifts are likely. Hysteresis effects within these materials, due to the rapidly changing field conditions (amplitude and direction) and the time required for the atomic dipoles to achieve alignment compared with the RF field's time rate of change will also impact the transmitting signal. Furthermore, objects of interest with geometries favorable to produce Eddy current loops will tend to have a stronger attenuating effect on the transmitted magnetic field. Techniques using injectable magnetic or conductive media can provide even further image enhancement.

In an alternative passive mode of operation (FIG. 6), the RF transmitting source is a structure known to produce an inductive field, like an alternating current-carrying wire or energized RF circuit. This RF magnetic field radiating object is placed in close proximity to the loop detector array which uses that received signal to produce the object's image. A schematic view of the passive mode of operation is shown in FIG. 6.

The primary function of the loop-shaped bolometer detector array is to convert the incident RF magnetic flux across a detection plane into an analog, spatially-dependent intensity signal map. Within the detector array, the bolometer device includes an uncooled resistive, loop-shaped (foil, wire, or trace) thermo-sensing element and signal conditioning circuitry. This loop-shaped, thermo-sensing element comprises a resistive material (e.g., metal, semiconductor, other) with a known temperature coefficient of resistance (TCR) and support structure. When the induced current is used directly, the loop material properties are selected to maximize the loop elements' receiving efficiency. Unlike most other magnetic imaging techniques which rely on nuclear resonance to produce an image, this system relies on flux density measurements at a location for image generation. As the magnetic field wave front departs the object of interest, the flux density at a point varies based on the extent it was affected by transmission through the object. When that spatially-varying RF magnetic flux impinges on the loop elements, currents proportional to the flux density are induced within the circumference of loop elements either resulting in Joule heating within the thermosensing layer that produces detectable resistance changes or can be directly amplified for further processing.

The loop spacing is optimized between capturing sufficient magnetic flux to ensure sufficient range of detection above the noise level of the bolometer circuit and image resolution, which is predominantly determined by the distance separating loops. The signal conditioning circuit leverages those typical of bolometer circuits, such as Wheatstone bridges or balancing amplifiers, that provide direct current biasing during operation and detect the resistance changes occurring within the thermosensing element. It should be appreciated that there may be previously undisclosed circuit configurations necessary for maximizing the sensitivity of the loop element.

Figure 12C:
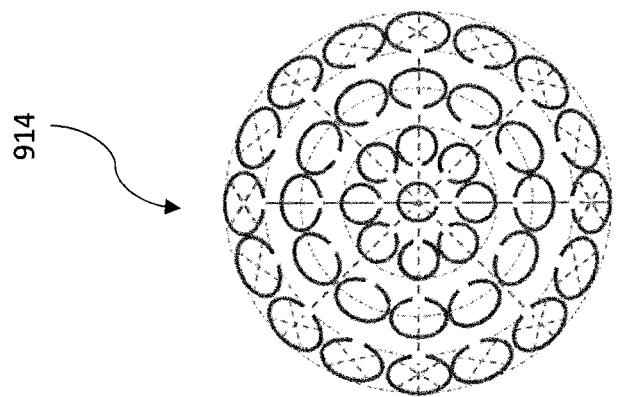
FIGS. 12A-12E are example embodiments of the array of RF antenna elements from the imaging device, according to the present disclosure.
Figure 12B:
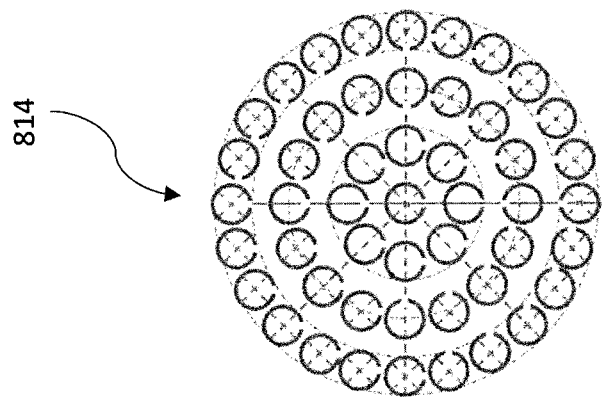
Figure 12A:
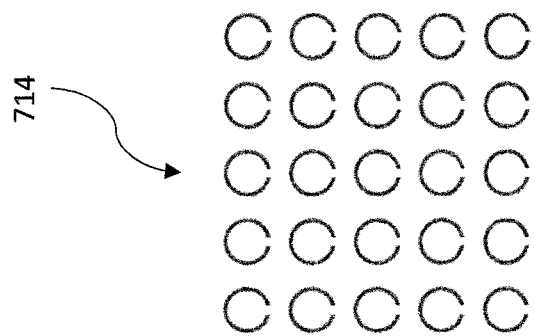
Figures 12D, 12E:
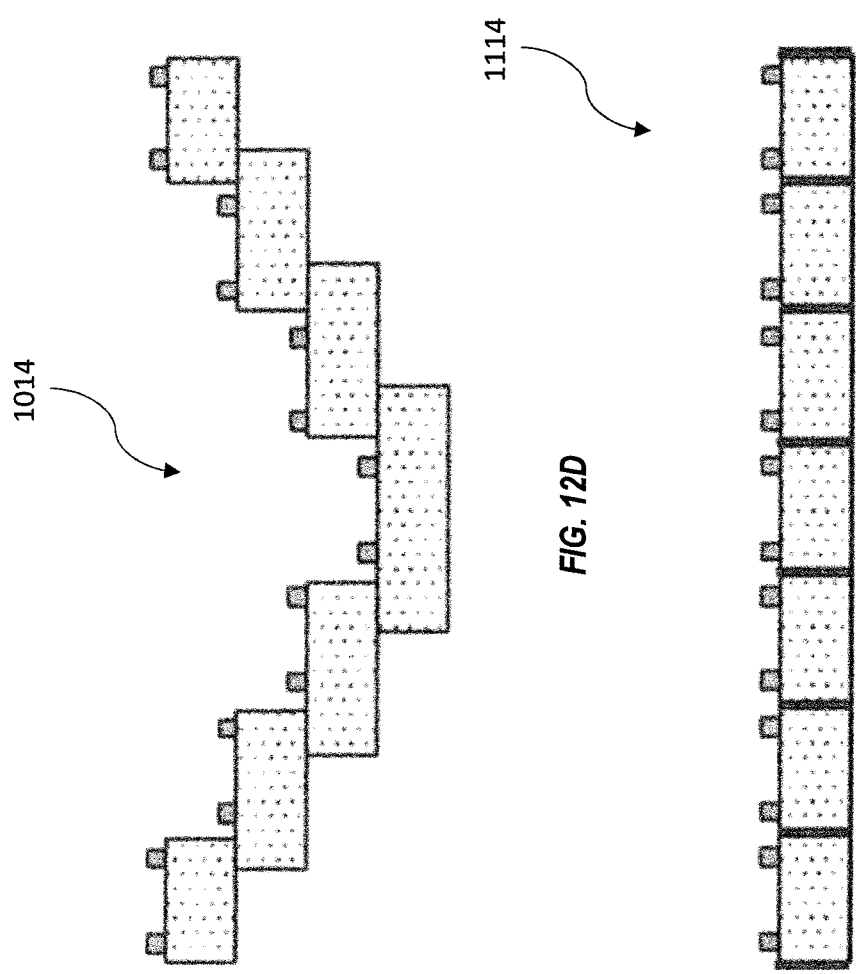

In addition, conversion of the loop's detected output into a signal used in image processing, phase matching, amplification, analog-to-digital conversion and/or location encoding may also be applied during this conditioning. The spatial arrangement of the loop elements is application and magnetic field source dependent and may be contoured to ensure similar incident field strength across the detector array (FIGS. 12A-12C). Element loop shapes are designed to efficiently capture as much of the incident RF magnetic flux passing through its location as possible while minimizing mutual coupling with an adjacent element which would reduce the detected signal strength. Possible approaches for improving the amount of incident RF magnetic field captured by allowing placement of the loops in closer proximity are shown in FIGS. 12D-12E. By changing the plane of adjacent loop elements, the added distance between the loop elements reduces their respective interaction. This approach is balanced against the drop in magnetic field strength caused by the increased distance from the RF field radiator. Another approach incorporates high permittivity regions between adjacent loop elements to increase their "electrical" separation.

The image processor combines the analog bolometer outputs while maintaining their spatial relationships into an image. That image is then manipulated and formatted for display. The image processor includes any circuitry necessary for combining the individual bolometer element outputs and for image conversion. This processing likely will leverage existing approaches but may require previously undisclosed techniques to ensure optimal image generation. Lastly, the display receives the processed image and presents it to the user.

In addition to the detector and sensor for RF magnetic field as described above, the present disclosure can be applied to RF waves, millimeter waves and the terahertz waves in the electromagnetic spectrum. The terahertz region is generally defined as the frequency range of 300 GHz (1 mm wavelength) to 3 THz (0.1 mm wavelength) in the electromagnetic spectrum. The operating mechanisms for detecting or sensing these waves and the RF magnetic field are based on scattering, transmission, reflection, diffraction and electromagnetic induction.

As a medical imager, the disclosed embodiments may produce MRI-like images of biological materials from a significantly more compact (or transportable/portable) and affordable system than existing MRI systems. In the active mode, the manner of image capture is similar to that used for X-ray imaging with a major benefit of the disclosed embodiments being that no radioactive source is needed to create an image, greatly reducing the hazards associated with its use.

As an RF probe used for nondestructive analysis of electronic circuits, the added resolution provided by the detector array versus existing RF probe technologies which use a single detection loop probe would improve the ability to isolate RF leakage locations and differentiate between radiation sources in closer proximity.

In the nondestructive analysis of objects and/or electronics circuits in the active mode, the present embodiments do not require submersion of the object into a fluid bath like acoustic microscopy requires enabling observation of active circuits, hermetic packages with air cavities, or objects that cannot be submerged. X-ray methods also require radioactive source and cannot typically detect delamination. The RF magnetic reflection that occurs at interfaces may make imaging of delaminated defects possible and as stated previously, eliminate the need for a radioactive source.

A potential application for the present disclosure is as a medical or scientific imager. A schematic view of its use as a medical imager is shown in FIG. 14. Biological tissue with slight conductivities on the order of 0.1-1.0 Siemens per meter (S/m) will have a slight effect on transmitted magnetic fields. Because hemoglobin has higher permeability due to its iron content, blood's effect on the transmitted magnetic fields is more significantly. Thus, visualization of blood vessels, clots, and internal hemorrhaging should be possible. In addition, any metallic shrapnel would be readily imaged. As a scientific imager (as shown in FIG. 5), detection of internal cracks or voids may be possible as well as visualization of permeability variations and magnetic domains. In a related application, this system could provide an imaging system for implanted medical device identification markings in the form of bar codes or other identifiable markings detectable utilizing the disclosed magnetic imaging method.

Another application is for the nondestructive analysis of electronic circuits. One potential approach involves utilizing the present disclosure in its active mode of operation with the circuit placed between a RF magnetic field radiator and the loop bolometer detector array as shown in FIG. 15. This technique would enable inspection of buried circuit layers for product verification and troubleshooting purposes. In the passive mode of operation (see FIG. 6), the loop bolometer array is used as an RF probe by positioning it in close proximity to an energized electronic circuit. This approach is used for confirming functionality, testing RF isolation, and for troubleshooting purposes, as well.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

REFERENCES (INCORPORATED BY REFERENCE IN THEIR ENTIRETY)

[1] S. Langley, "The Bolometer and Radiant Energy," Proceedings of the American Academy of Arts and Sciences, 16, 384-358, (1881).
[2] P. L. Richards, "Bolometers for Infrared and Millimeter Waves," Journal of Applied Physics, 76 (1) 1-24, (1994).
[3] E. Peskin and E. Weber, "The D.C. Thermal Characteristics of Microwave Bolometers," Review of Scientific Instruments, 19 (3), 188-195 (1948).
[4] J. F. Byrne and C. F. Cook, "Microwave Type Bolometer for Submillimeter Wave Measurements," in IEEE Millimeter and Submillimeter Conference, Orlando, Fla., (1963).
[5] P. W. Kruse, "A Comparison of the Limits to the Performance of Thermal and Photon Detector Arrays," Infrared Physics & Technology, 36, 869-882, (1995).
[6] A. Kar, R. Vaidyanathan and J. M. Jennnings, "RF magnetic field imaging using loop bolometer array". USA Patent UCF REF #11287, 27 Feb. 2018.
[7] M. Elmaoglu and A. Celik, [MRI Handbook: MRI Physics, Patient Positioning, and Protocals], Springer Science+Business Media, LLC., New York, N.Y., 7-17 (2012).
[8] S. Gloggler, R. Blumich and S. Appelt, "NRM Spectroscopy for Chemical Analysis at Low Magnetic Fields," Topics in Current Chemistry, 335, 1-22, (2013).
[9] J. Nyenhuis, "MRI Interactions with Medical Implants," in IEEE International Symposium on Electromagnetic Compatibility, Minneapolis, Minn., 920-924 (2002).
[10] J. A. Nyenhuis, S.-M. Park, R. Kamondetdacha, A. Amjad, F. G. Shellock and A. R. Rezai, "MRI and Implanted Medical Devices: Basic Interactions with an Emphasis on Heating," IEEE Transactions on Device and Materials Reliability, 5 (3), 467-480, (2005).

[11] Design and Selector Guide for High Precision Resistors. Vishay, (2015).

[12] A. Kosarev, A. Torres and M. Moreno, "Thin Film Micro-Bolometers with Si—Ge Thermo-Sensing Films Deposited from Plasma Discharge," [Bolometers: Theory, Types and Applications], Nova Science Publishers, Inc., New York, 1-82, (2010).

[13] F. M. Greene, "The Near-Zone Magnetic Field of a Small Circular-Loop Antenna," Journal of Research of the Nathional Bureau of Standards-C. Engineering and Instrumentation, 71C, 319-326, (1967).

That which is claimed is:

1. An imaging device comprising:
a radio frequency (RF) source configured to irradiate an object with RF radiation;
an array of RF antenna elements, each RF antenna element comprising a loop bolometer configured to receive the RF radiation after interaction with the object;
a processor configured to generate an image based upon respective outputs from said array of RF antenna elements; and
a display coupled to said processor and configured to display the image of the object.

2. The imaging device of claim 1 wherein said processor is configured to generate the image of the object based upon detected spatial variation of flux density for the RF radiation.

3. The imaging device of claim 1 wherein each loop bolometer is configured to receive the RF radiation emitted by the object during irradiation of the object with said RF source.

4. The imaging device of claim 1 wherein each loop bolometer comprises a resistive loop; and wherein each RF antenna element comprises a signal conditioning circuit coupled to said resistive loop.

5. The imaging device of claim 4 wherein said signal conditioning circuit is configured to pass a sensing current through said resistive loop.

6. The imaging device of claim 4 wherein each RF antenna element comprises a capacitor coupled between ends of said resistive loop.

7. The imaging device of claim 4 wherein said signal conditioning circuit comprises a plurality of resistors coupled as a resistor bridge.

8. The imaging device of claim 1 wherein said RF source is configured to generate the RF radiation within a frequency range of 30 to 130 MHz.

9. The imaging device of claim 1 wherein each loop bolometer is configured to receive the RF radiation emitted by the object without irradiation of the object with said RF source.

10. An imaging device comprising:
an object configured to emit RF radiation;
an array of RF antenna elements, each RF antenna element comprising a loop bolometer configured to receive the RF radiation from the object; and
a processor configured to generate an image based upon respective outputs from said array of RF antenna elements.

11. The imaging device of claim 10 wherein said processor is configured to generate the image of the object based upon detected spatial variation of flux density for the RF radiation.

12. The imaging device of claim 10 wherein each loop bolometer is configured to receive the RF radiation emitted by the object when the object is energized.

13. The imaging device of claim 10 wherein each loop bolometer comprises a resistive loop; and wherein each RF antenna element comprises a signal conditioning circuit coupled to said resistive loop.

14. The imaging device of claim 13 wherein said signal conditioning circuit is configured to pass a sensing current through said resistive loop.

15. The imaging device of claim 13 wherein each RF antenna element comprises a capacitor coupled between ends of said resistive loop.

16. The imaging device of claim 13 wherein said signal conditioning circuit comprises a plurality of resistors coupled as a resistor bridge.

17. The imaging device of claim 10 wherein said RF source is configured to generate the RF radiation within a frequency range of 30 to 130 MHz.

18. A method for making an imaging device comprising:
positioning a radio frequency (RF) source configured to irradiate an object with RE radiation;
positioning an array of RF antenna elements, each RF antenna element comprising a loop bolometer configured to receive the RF radiation after interaction with the object;
coupling a processor configured to generate an image based upon respective outputs from the array of RF antenna elements; and
coupling a display to the processor and configured to display the image of the object.

19. The method of claim 18 wherein the processor is configured to generate the image of the object based upon detected spatial variation of flux density for the RF radiation.

20. The method of claim 18 wherein each loop bolometer is configured to receive the RF radiation emitted by the object during irradiation of the object with the RF source.

* * * * *